United States Patent
Nozawa

(10) Patent No.: US 10,250,815 B2
(45) Date of Patent: Apr. 2, 2019

(54) COMPONENT MOUNTER INCLUDING A NOZZLE, CAMERA, AND A TRANSFER DEVICE

(71) Applicant: FUJI CORPORATION, Chiryu (JP)

(72) Inventor: Tatsuji Nozawa, Toyokawa (JP)

(73) Assignee: FUJI CORPORATION, Chiryu (JP)

( * ) Notice: Subject to any disclaimer, the term of this patent is extended or adjusted under 35 U.S.C. 154(b) by 152 days.

(21) Appl. No.: 14/785,384

(22) PCT Filed: May 13, 2013

(86) PCT No.: PCT/JP2013/063331
§ 371 (c)(1),
(2) Date: Oct. 19, 2015

(87) PCT Pub. No.: WO2014/184855
PCT Pub. Date: Nov. 20, 2014

(65) Prior Publication Data
US 2016/0100089 A1  Apr. 7, 2016

(51) Int. Cl.
H04N 5/235 (2006.01)
G01N 21/956 (2006.01)
(Continued)

(52) U.S. Cl.
CPC ......... *H04N 5/2353* (2013.01); *G01N 21/956* (2013.01); *G06T 7/0004* (2013.01); *H05K 13/0817* (2018.08); *G06T 2207/30152* (2013.01)

(58) Field of Classification Search
CPC .. H04N 5/2353; G01N 21/956; G06T 7/0004; G06T 2207/30152; H05K 13/08
(Continued)

(56) References Cited

U.S. PATENT DOCUMENTS

| 2002/0138974 A1* | 10/2002 | Suhara | H05K 13/08 29/740 |
| 2008/0197170 A1* | 8/2008 | Prince | G01N 21/8806 228/103 |
| 2009/0161913 A1* | 6/2009 | Son | G06K 9/00771 382/105 |

FOREIGN PATENT DOCUMENTS

| JP | 2008 216140 | 9/2008 |
| JP | 2008-235739 A | 10/2008 |
| JP | 2008235739 A * | 10/2008 |

OTHER PUBLICATIONS

International Search Report dated Jul. 16, 2013 in PCT/JP13/063331 Filed May 13, 2013.
(Continued)

*Primary Examiner* — Jamie J Atala
*Assistant Examiner* — Ayman A Abaza
(74) *Attorney, Agent, or Firm* — Oblon, McClelland, Maier & Neustadt, L.L.P.

(57) ABSTRACT

Component mounter includes a transfer inspection device that inspects the transfer state of solder by imaging the bottom surface of a component, and a transfer inspection data creation device that creates transfer inspection data. The transfer inspection data creation device performs imaging of the bottom surface of a pre-transfer component with a camera at multiple shutter speeds, acquires the multiple pre-transfer images of different shutter speeds, obtains pre-transfer bump portion pixel values, performs imaging of the bottom surface of a post-transfer component with the camera at the same multiple shutter speeds, acquires the multiple post-transfer images of different shutter speeds, obtains post-transfer bump portion pixel values, and determines the shutter speed to be used when performing transfer inspection based on the post-transfer bump portion pixel values. Transfer inspection data is created based on the pre- and post-
(Continued)

transfer bump portion pixel values of images captured at the determined shutter speed.

6 Claims, 6 Drawing Sheets

(51) Int. Cl.
*G06T 7/00* (2017.01)
*H05K 13/08* (2006.01)
(58) Field of Classification Search
USPC .......................................................... 348/95
See application file for complete search history.

(56) References Cited

OTHER PUBLICATIONS

Extended European Search Report dated Apr. 21, 2016 in Patent Application No. 13884704.1.
Office Action dated May 17, 2017 in Chinese Patent Application No. 201380076519.1 (English translation only).

* cited by examiner

[Fig. 1]
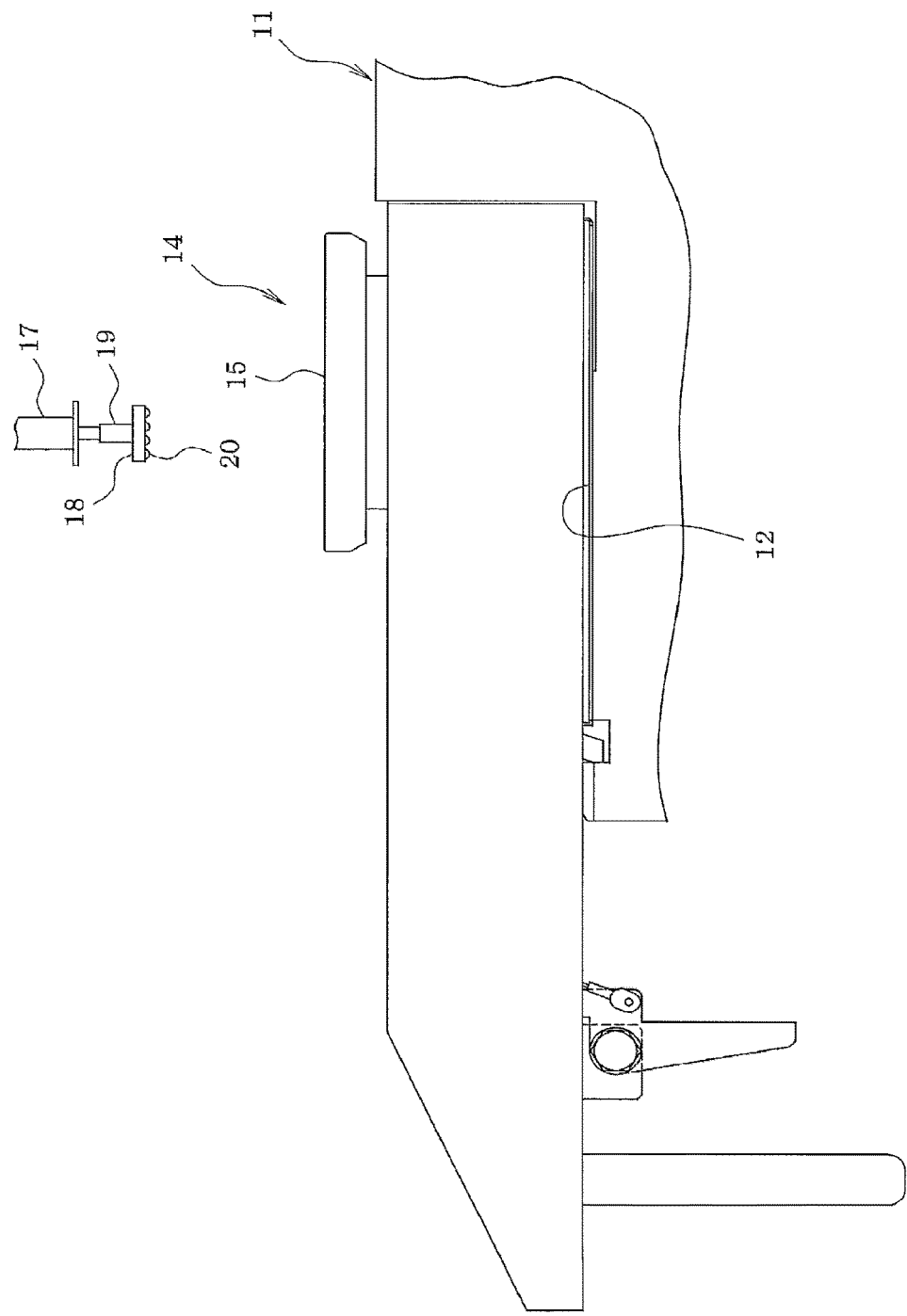

[Fig. 2]
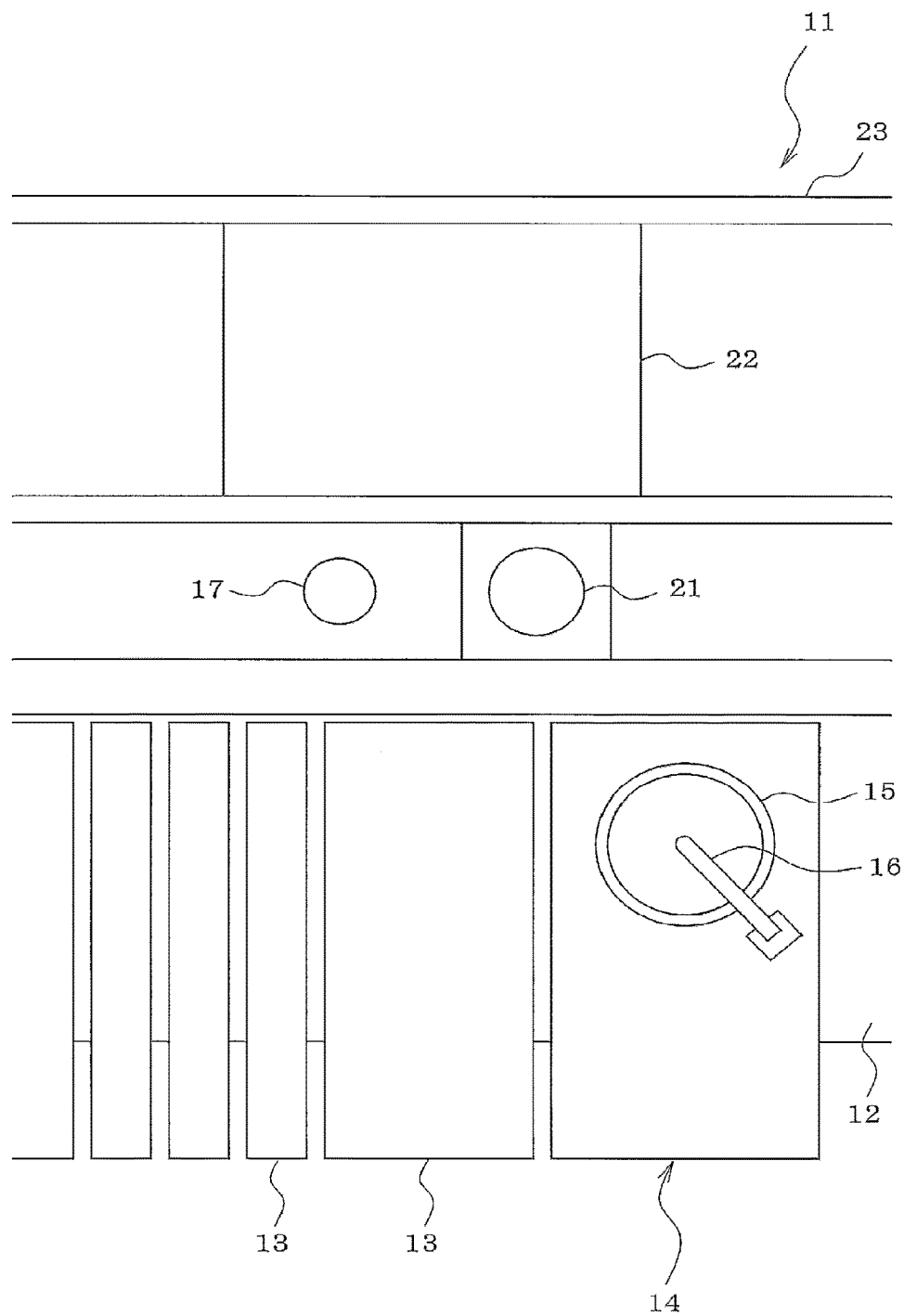

[Fig.3]
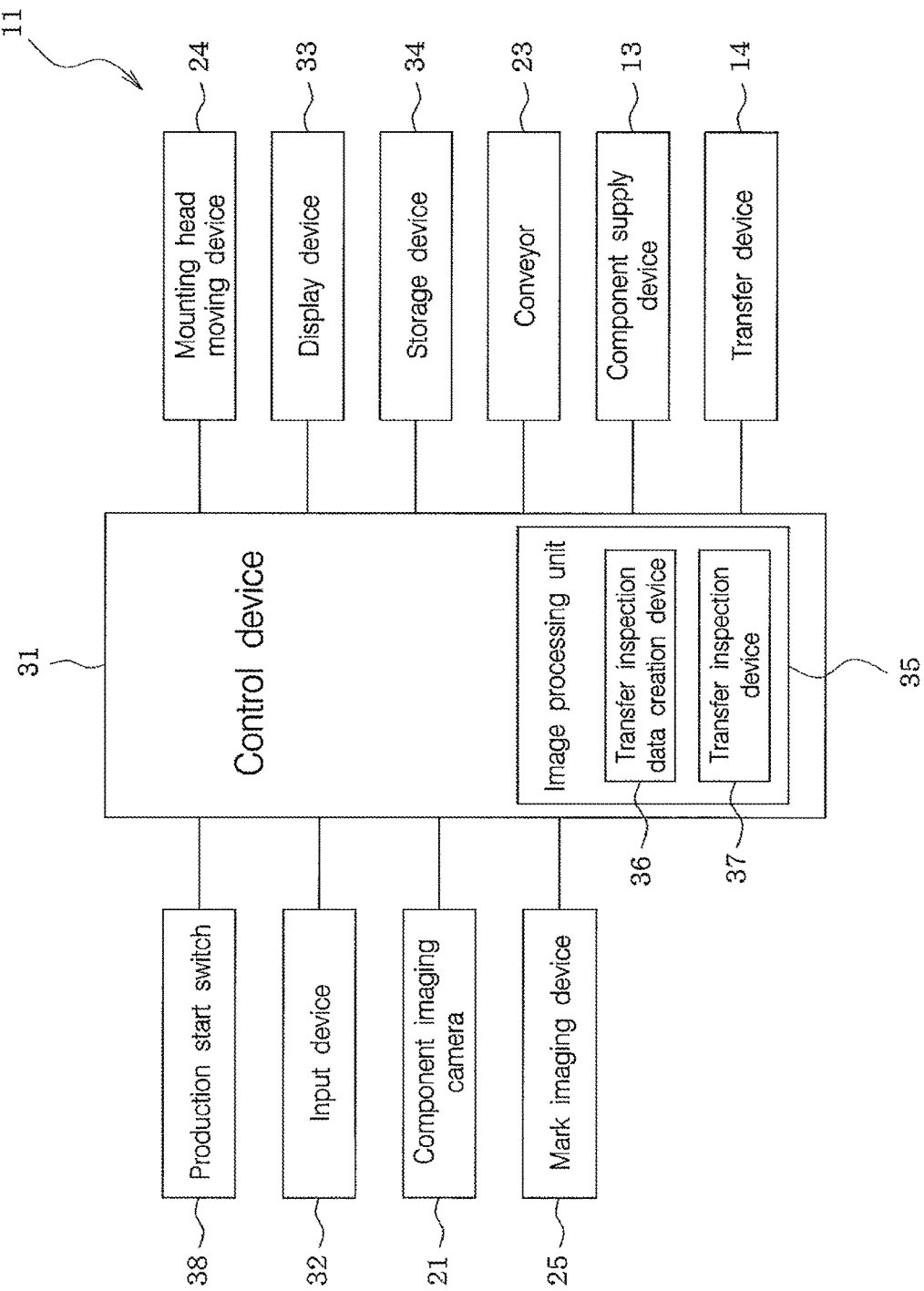

[Fig.4]
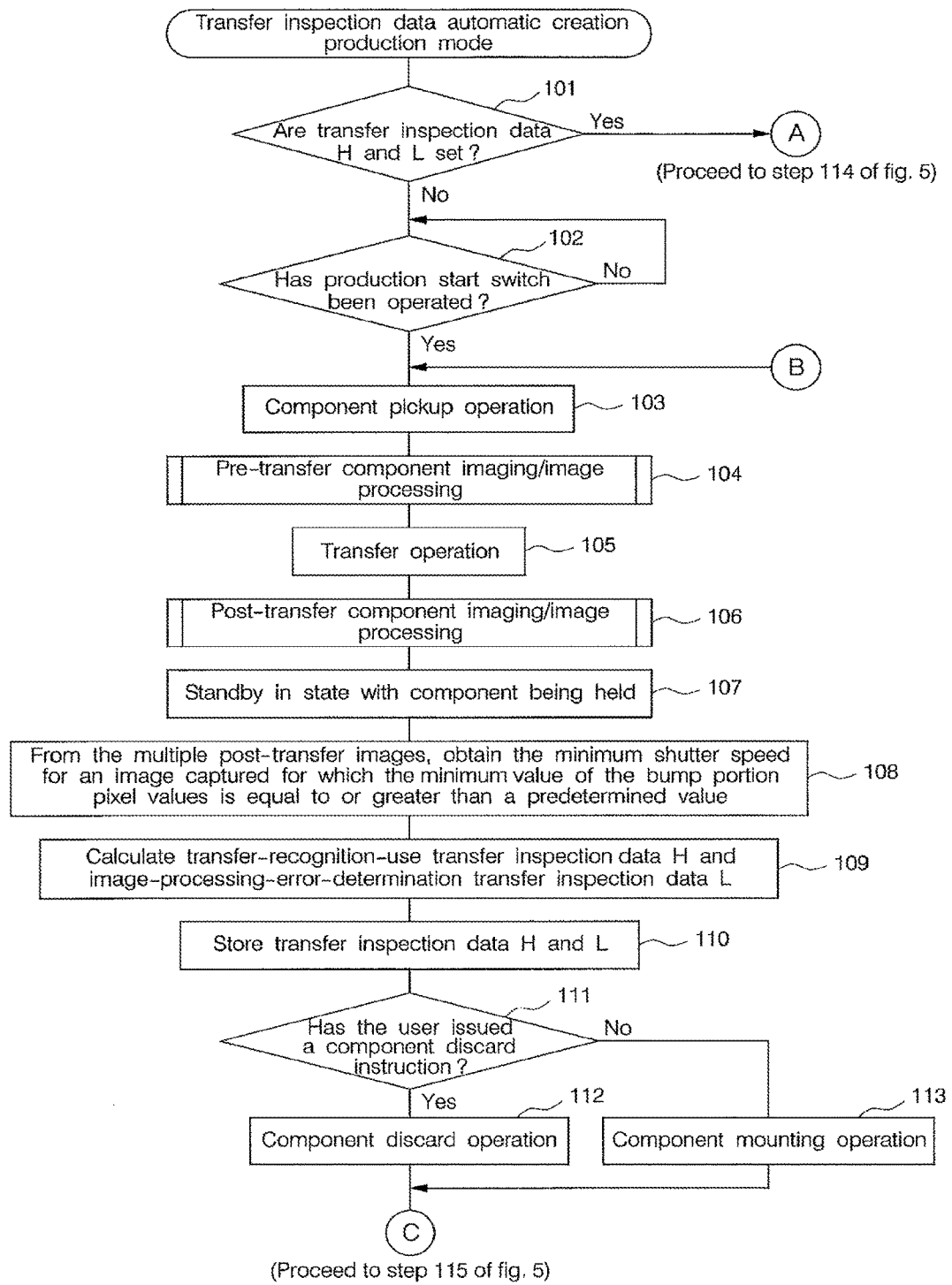

[Fig.5]
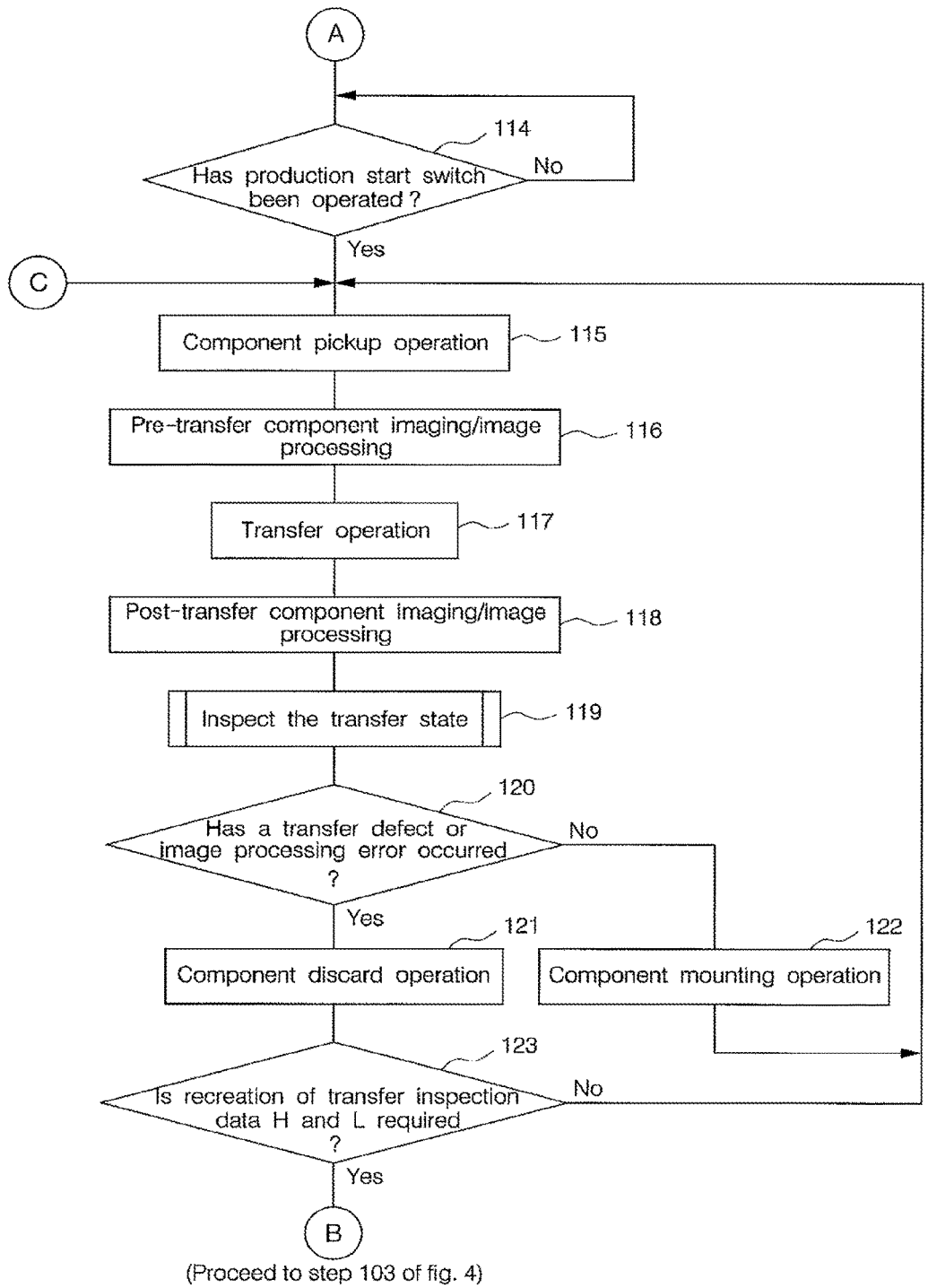
(Proceed to step 103 of fig. 4)

[Fig.6]
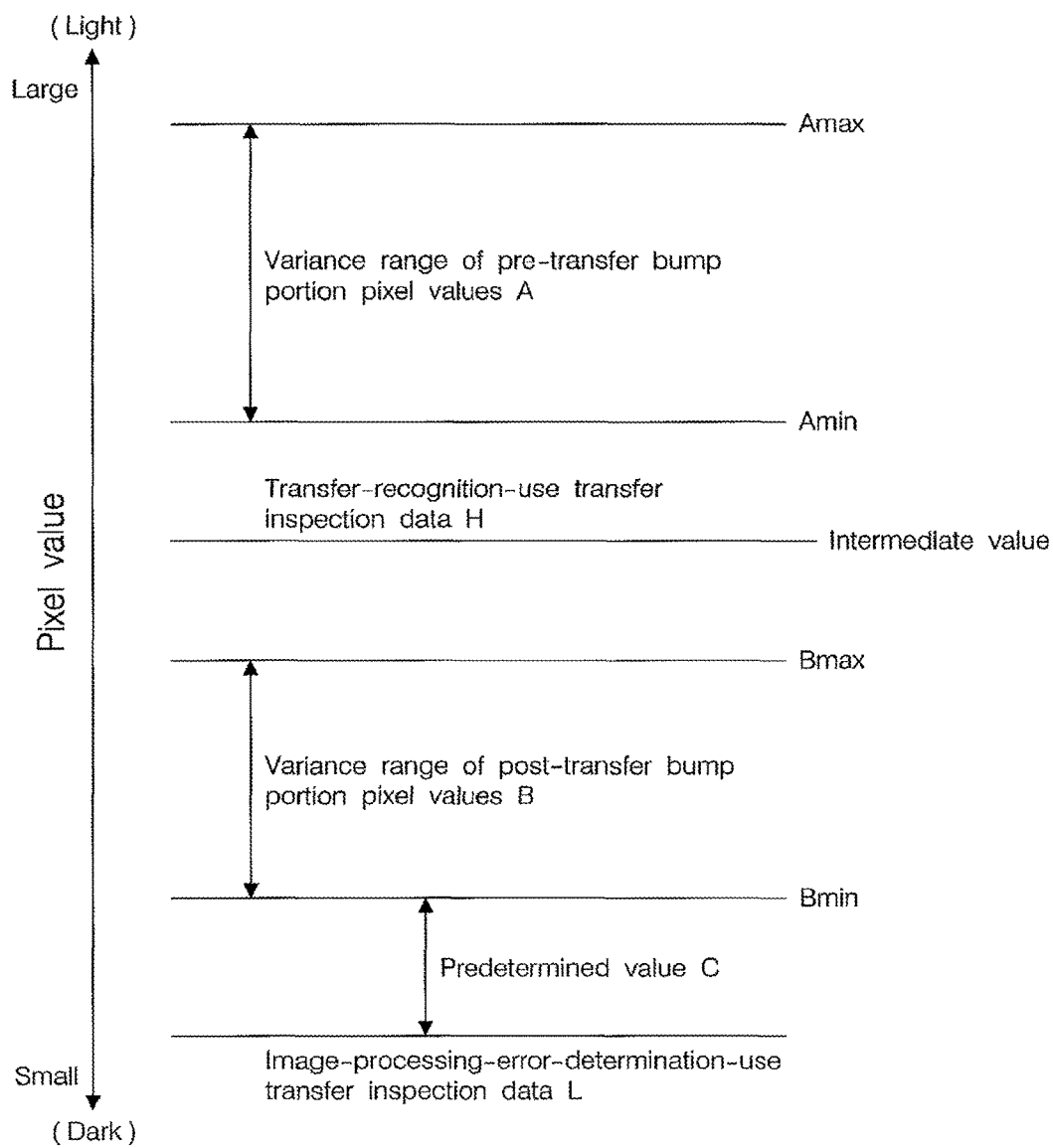

COMPONENT MOUNTER INCLUDING A NOZZLE, CAMERA, AND A TRANSFER DEVICE

TECHNICAL FIELD

The present disclosure relates to a component mounter provided with a function that inspects the transfer state of solder or flux which has been transferred onto the bumps on the bottom surface of a component by imaging the bottom surface of the component held by a suction nozzle with a camera and performing image recognition.

BACKGROUND ART

For example, when mounting a component on which bumps (protruding sections of a conductor, terminals, electrodes) are formed on the bottom surface thereof onto a board or a pre-mounted component, there are cases in which the component is mounted after transferring solder or flux (hereafter these are referred to as "solder or the like") on the bumps on the bottom surface of the component being held by a suction nozzle. In this case, because a mounting defect will occur if the transfer state of the solder or the like onto the bumps is defective, in the component mounter disclosed in patent literature 1 (JP-A-2008-216140), the bottom surface of the component held by the suction nozzle is imaged, the pixel values (brightness) of the bump portion of the component bottom surface captured in the image are measured, and those pixel values are compared with transfer inspection data (threshold values for transfer inspection), such that inspection is performed to determine good/bad solder transfer.

Conventionally, when creating transfer inspection data, the component bottom surface is imaged by the camera of the component mounter both before and after solder or the like is transferred to the bumps of the component held by a suction nozzle of a component mounter, the images thereof are downloaded to an offline data creation device provided externally to the component mounter, an operator uses the offline data creation device to manually create the transfer inspection data while visually checking the pixel values for each bump, then transmits that transfer inspection data to the component mounter such that inspection is performed for good/bad solder transfer at the component mounter using the transfer inspection data.

CITATION LIST

Patent Literature

Patent Literature 1: JP-A-2008-216140

SUMMARY

Problem to be Solved

However, the pixel values of the image captured of the component bottom surface change depending on the lighting conditions and shutter speed (exposure time) of the camera. For example, for the same imaging target, the slower the shutter speed, the larger the pixel value; and the brighter the lighting, the larger the pixel value. Because the lighting conditions are decided according to the lighting device of the camera for each component mounter, it is necessary to decide an appropriate shutter speed for recognizing the transfer state for each component mounter, and the transfer inspection data must also be changed according to that shutter speed.

Conventionally, when creating transfer inspection data for multiple shutter speeds, a pre- and post-transfer image is taken for each shutter speed with the camera, and for the capturing of a pre- and post-transfer image for each shutter speed, the component mounter is stopped, the pre- and post-transfer images are downloaded to the offline creation device, the imaged component is discarded, the shutter speed is changed, a new component is picked up by the suction nozzle, and a pre- and post-transfer image is captured by the camera, with this processing being repeated. Due to this, not only does the creation of transfer inspection data take a lot of work and time, components must be discarded each time the shutter speed is changed, thereby increasing the cost. Further, because there is variance in the lighting conditions between component mounters, it is necessary to create transfer inspection data for each component mounter to absorb this variance in lighting conditions. Due to this, the above problems related to the creation of transfer inspection data are exacerbated as the quantity of component mounters that have a transfer inspection function increases.

Therefore, to solve the above problems, the present disclosure is a component mounter that can greatly reduce the work and time for creating transfer inspection data, and that can make the discard quantity of components used when creating transfer inspection data zero or one only.

Means of Solving the Problem

To solve the above problems, the present disclosure is a component mounter provided with a transfer inspection device that inspects the transfer state of a fluid, which is one of solder, flux, conductive paste, or adhesive, which has been transferred onto the bumps (protruding sections of a conductor, terminals, electrodes) on the bottom surface of a component by imaging the bottom surface of the component held by a suction nozzle with a camera and performing image recognition, comprising: a transfer inspection data creation device that creates transfer inspection data used when inspecting the transfer state of the fluid, wherein the transfer inspection data creation device includes an image processing means that performs imaging with the camera of the bottom surface of the component being held by the suction nozzle before the fluid has been transferred to the bumps on the bottom surface of the component at multiple shutter speeds, then acquires the multiple pre-transfer images captured at different shutter speeds, and determines the pixel values of the pre-transfer bump portions by performing gray processing on each pre-transfer image, and that also performs imaging with the camera of the bottom surface of the component after the fluid has been transferred to the bumps on the bottom surface of the component at the same multiple shutter speeds as pre-transfer, then acquires the multiple post-transfer images captured at different shutter speeds, and determines the pixel values of the post-transfer bump portions by performing gray processing on each post-transfer image; a shutter speed determining means that determines the shutter speed used for inspection of the transfer state based on the pixel values of the post-transfer bump portions; and a transfer inspection data creation means that creates the transfer inspection data based on the pixel values of the post-transfer bump portions of the image captured with the shutter speed determined by the shutter speed determining means.

With this configuration, because the transfer inspection data creation device is provided on the component mounter, the transfer inspection data creation device automatically determines the shutter speed used for inspecting the transfer state, and the transfer inspection data is created based on the pixel values of the pre- and post-transfer bump portions of the images captured at that shutter speed, the work and time for creating transfer inspection data can be greatly reduced and even an operator not knowledgeable in the creation method of transfer inspection data can easily create transfer inspection data. Further, as well as it being possible to acquire multiple pre-transfer images and multiple post-transfer images at multiple different shutter speeds without discarding the one component used for creating transfer inspection data, it is possible to use the component used for creating transfer inspection data as is in production, so the component discard quantity can be zero or one only. Also, even if the quantity of component mounters that have a transfer inspection function increases, it is possible to easily create transfer inspection data that absorbs the variance in lighting conditions between each component mounter.

For the present disclosure, when determining the shutter speed to be used for inspecting the transfer state, the shutter speed may be determined as the minimum shutter speed from the shutter speeds for which the minimum value for the pixel values of the post-transfer bump portion for the captured images was equal to or larger than a predetermined value. In this way, the shutter speed can be minimized within a range in which the ability to recognize the transfer state is maintained, thus meeting the demand for high speed image processing.

Also, the transfer inspection data creation means may calculate an intermediate value between the minimum value of the pixel values of the pre-transfer bump portion and the maximum value of the pixel values of the post-transfer bump portion of the images captured at the shutter speed determined by the shutter speed determining means to be used as transfer-recognition-use transfer inspection data, and the transfer inspection device may use the transfer-recognition-use transfer inspection data as a threshold value for determining fluid transfer portions and fluid non-transfer portions (portions where a bump is exposed). If an intermediate value between the minimum value of the pixel values of the pre-transfer bump portion and the maximum value of the pixel values of the post-transfer bump portion is used as transfer-recognition-use transfer inspection data in this way, the difference in the transfer-recognition-use transfer inspection data and the variance range of the pixel values of the pre- and post-transfer bump portion can be made uniformly large, thus the fluid transfer portions and fluid non-transfer portions can be recognized with good accuracy.

Also, the transfer inspection data creation means may calculate a value which is smaller than the minimum value of the pixel values of the post-transfer bump portion of the image captured at the shutter speed determined by the shutter speed determining means by a predetermined value as image-processing-error-determination-use transfer inspection data, and the transfer inspection device may use the image-processing-error-determination-use transfer inspection data as a threshold value for determining image processing errors. In this way, image-processing-error-determination-use transfer inspection data which determines whether an image processing error has occurred can be created automatically.

Also, the transfer inspection data creation device, in cases in which production is performed using components onto which fluid is transferred, may create transfer inspection data when the transfer inspection data has not been created. This is so that production can be started after automatically creating transfer inspection data in cases in which the transfer inspection data required for production has not been created.

In other words, the transfer inspection data creation device may recreate transfer inspection data when the transfer inspection device determines that a transfer defect or image processing error has occurred during production using a component onto which fluid is transferred. This is because that, for cases in which transfer defects or image processing errors have been determined falsely due to deviation in the transfer inspection data, there are cases in which false determinations of transfer defects or image processing errors can be avoided by the transfer inspection data being modified by recreating the transfer inspection data.

BRIEF DESCRIPTION OF DRAWINGS

FIG. 1 is a side view showing an embodiment of the present disclosure in a state in which a transfer device is set in the component mounter.

FIG. 2 is a plan view showing conceptually the configuration of the main elements of the component mounter.

FIG. 3 is a block diagram showing the configuration of the control system of the component mounter.

FIG. 4 is a flowchart (number one) showing the processing flow of the program of transfer inspection data automatic creation production mode.

FIG. 5 is a flowchart (number two) showing the processing flow of the program of transfer inspection data automatic creation production mode.

FIG. 6 illustrates the size relationship between the variance range of pixel values A and B of the pre- and post-transfer bump portion, and transfer-recognition-use/image-processing-error-determination-use transfer inspection data H and L.

DESCRIPTION OF EMBODIMENT

An embodiment is described below.

The configuration of the component mounter is described using FIGS. 1 to 3.

As shown in FIG. 1 and FIG. 2, component supply devices 13 such as a tape feeder or tray feeder and a transfer device 14 are detachably set adjacent to each other on set table 12 of component mounter 11. Disc-shaped rotation table 15 (transfer table) that forms solder (fluid) into a film is detachably mounted on the transfer device 14, and the rotation table 15 is rotated by a motor (not shown).

As shown in FIG. 2, squeegee 16 with a length almost the same as the radius of the rotation table 15 is provided above the rotating table 15 along the direction of the radius, and by rotating rotation table 15, the solder in rotation table 15 is spread evenly and formed into a film by squeegee 16.

As shown in FIG. 1, suction nozzle 19 for picking up component 18 supplied from component supply device 13 is exchangeably held on mounting head 17 of component mounter 11. During operating of component mounter 11, in cases in which the component 18 picked up by suction nozzle 19 is a component to which solder is to be transferred (such as a BGA component or chip component), by moving the component 18 above rotation table 15 of transfer device 14 and then lowering component 18, each bump 20 (protruding section of a conductor, terminal, electrode) on the bottom surface of component 18 is dipped into the solder film in rotation table 15, thereby transferring solder to each bump 20.

As shown in FIG. 2, component imaging camera 21 that images from below the component 18 held by the suction nozzle 19 is provided on component mounter 11 at a position below the path on which suction nozzle 19 of mounting head 17 moves. Conveyor 23 for conveying circuit board 22, mounting head moving device 24 (see FIG. 3) that moves mounting head 17 in the XY direction (the board conveyance direction and the direction perpendicular thereof), and the like are also provided on component mounter 11. Mark imaging camera 25 (see FIG. 3) that images reference position marks (not shown) of circuit board 22 is loaded on mounting head 17.

As shown in FIG. 3, input devices 32 such as a keyboard, a mouse, and a touch panel; display devices 33 such as a liquid crystal display, and CRT; and a storage device 34 that stores each data and programs of the transfer inspection data automatic creation production mode of FIG. 4 and FIG. 5 described below, are connected to control device 31 of component mounter 11. Further, image processing unit 35 that processes images captured by component imaging camera 21 and mark imaging camera 25 is embedded in control device 31. This imaging processing unit 35 functions as transfer inspection data creation device 36 that inspects the solder transfer state of each bump 20 portion of the bottom surface of component 18, and also functions as transfer inspection device 37 that creates transfer inspection data used when inspecting the solder transfer state.

During the operation of component mounter 11, control device 31 controls the operation of suction nozzle 19 picking up component 18 supplied from component supply unit 13 and the mounting of component 18 on circuit board 22. Here, in cases in which the component 18 picked up by suction nozzle 19 is a component to which solder is to be transferred such as a BGA component, by moving the component 18 held by suction nozzle 19 above rotation table 15 of transfer device 14 and then lowering component 18, component 18 is mounted on circuit board 22 after solder has been transferred to each bump on the bottom surface of component 18.

While component 18 held by suction nozzle 19 is being moved to a point above circuit board 22 (in cases in which component 18 is a component to which solder is to be transferred, after solder transfer has occurred), an image of component 18 is captured by component imaging camera 21, and this component image is processed in image processing unit 35 to determine the pickup orientation of component 18, the presence/absence of component 18, and the like. Here, in cases in which component 18 imaged by component imaging camera 21 is a solder transfer component, gray processing is performing on the image captured by component imaging camera 21 after solder transfer to recognize each bump portion 20 on the bottom surface of component 18, the pixel values (gray values) of each bump 20 portion are compared with transfer-recognition-use transfer inspection data H described below, with inspection for good/bad solder transfer performed based on whether the pixel values for each bump 20 portion are the same or smaller than transfer-recognition-use transfer inspection data H. During this inspection, in cases in which the pixel values of each bump 20 portion are the same or smaller than image-processing-error-determination-use transfer inspection data, it is determined that an image processing error has occurred.

Next, the function of transfer inspection data creation device 36 of image processing unit 35 is described. This function is realized as described below by the program of transfer inspection data automatic creation production mode of FIG. 4 and FIG. 5. The program of transfer inspection data automatic creation production mode of FIG. 4 and FIG. 5 is performed by control device 31 which includes image processing unit 35 when the production mode is set as a production mode for mounting solder transfer components and transfer inspection data automatic creation mode. The image-processing-use component data required for image recognition of each bump 20 on the bottom surface of component 18 held by suction nozzle 19 is stored in advance in storage device 34.

When the program of transfer inspection data automatic creation production mode is started, first, in step 101, it is determined whether, with regard to solder transfer components to be used in production, transfer-recognition-use/image-processing-error-determination-use transfer inspection data H and L are set; if it is determined that transfer inspection data H and L are not set, processing from step 102 is performed such that transfer inspection data H and L are created automatically as given below.

In step 102, it is determined whether an operator has operated production start switch 38 (refer to FIG. 3), and if it is determined that production start switch 38 has not been operated, the state becomes standby until that operation is performed. Then, at the point when an operator operates production start switch 38, processing continues to step 103, component 18 is picked up by suction nozzle 19 and the component 18 is moved to within the field of view of component imaging camera 21.

Then, continuing to step 104, pre-transfer component imaging/image processing are performed multiple times. In this pre-transfer component imaging/image processing, imaging of the bottom surface of pre-transfer component 18 held by suction nozzle 19 is performed by component imaging camera 21 at multiple shutter speeds, multiple pre-transfer images at different shutter speeds are acquired, gray processing is performed on each image and pre-transfer bump 20 portion pixel values are obtained and stored in storage device 34. At this stage, because the optimal shutter speed is unknown, the shutter speed is changed from an initial value (lower limit or lower limit shutter speed) to an upper limit or upper limit shutter speed in order at predetermined intervals with component imaging/image processing being performed at each shutter speed.

Then, continuing to step 105, after solder has been transferred to each bump 20 on the bottom surface of component 18 by component 18 held by suction nozzle 19 being moved above rotation table 15 of transfer device 14 and then being lowered, component 18 is moved within the field of view of component imaging camera 21. Then, continuing to step 106, post-transfer component imaging/image processing are performed multiple times. In this post-transfer component imaging/image processing, imaging of the bottom surface of post-transfer component 18 held by suction nozzle 19 is performed by component imaging camera 21 at the same multiple shutter speeds as for pre-transfer, multiple post-transfer images at different shutter speeds are acquired, gray processing is performed on each image and post-transfer bump 20 portion pixel values are obtained and stored in storage device 34. At this stage too, because the optimal shutter speed is unknown, the shutter speed is changed from an initial value (lower limit or lower limit shutter speed) to an upper limit or upper limit shutter speed in order at predetermined intervals with component imaging/image processing being performed at each shutter speed. The processing of steps 104 and 106 performs the role of the image processing means of the claims.

After this, while maintaining the state of component 18 being held by suction nozzle 19 (step 107), processing continues to step 108, wherein, from the multiple post-transfer images, images are selected for which the minimum pixel value for a bump 20 portion is equal to or greater than a predetermined value (for example, 100 or greater), the minimum shutter speed from the shutter speeds used to capture those images is obtained, and that shutter speed is determined as the shutter speed to be used for inspecting the transfer state. The processing of step 108 performs the role of the shutter speed determining means of the claims.

Then, continuing to step 109, transfer-recognition-use transfer inspection data H and image-processing-error-determination-use transfer inspection data L are calculated based on pixel values A and B of pre- and post-bump portions of images captured at the shutter speed determined in step 108.

Specifically, transfer-recognition-use transfer inspection data H is calculated as an intermediate value of minimum value Amin of pixel values A of pre-transfer bump 20 portions of images captured at the shutter speed determined in step 108 and maximum value Bmax of pixel values B of post-transfer bump 20 portions of images captured at the shutter speed determined in step 108.

Transfer-recognition-use transfer inspection data
$H=(A\text{min}+B\text{max})/2$ This transfer-recognition-use transfer inspection data H is used as the threshold value for distinguishing between solder transfer portions and solder non-transfer portions (portions where bump 20 is exposed). As shown in FIG. 6, because the variance range of pre-transfer bump 20 portion pixel value A is larger than the variance range of post-transfer bump 20 portion pixel value B, minimum value Amin of pre-transfer bump 20 portion pixel value A is larger than maximum value Bmax of post-transfer bump 20 portion pixel value B. It follows that, if an intermediate value between the minimum value Amin of the pixel values of the pre-transfer bump 20 portion images and the maximum value Bmax of the pixel values of the post-transfer bump 20 portion images is used as transfer-recognition-use transfer inspection data H, the difference in the transfer-recognition-use transfer inspection data H and the variance range of the pixel values A and B of the pre- and post-transfer bump 20 portion can be made uniformly large, such that the solder transfer portions and solder non-transfer portions (portions where bump 20 is exposed) can be recognized with good accuracy.

Also, a value that is smaller by predetermined value C (for example, 15) than minimum value Bmin of post-bump 20 portions pixel values B of the image captured at the shutter speed determined in step 108 is calculated as image-processing-error-determination-use transfer inspection data L.

Image-processing-error-determination-use transfer
inspection data $L=B\text{min}-C$ This image-processing-error-determination-use transfer inspection data L is used as the threshold value for determining image processing errors. During production, if the post-transfer bump 20 portion pixel value is equal to or smaller than image-processing-error-determination-use transfer inspection data L, this means that foreign matter darker than solder is attached to bump 20, the lighting illuminating the bottom surface of component 19 is dark, component imaging camera 21 is damaged, or some other problem has occurred, therefore if during production the post-transfer bump 20 portion pixel value is equal to or smaller than image-processing-error-determination-use transfer inspection data L, an image processing error is determined to have occurred. The processing of step 109 performs the role of the transfer inspection data creation means of the claims.

After transfer-recognition-use/image-processing-error-determination-use transfer inspection data H and L have been calculated as above, processing continues to step 110 and these transfer inspection data H and L are stored in storage device 34. Then, continuing to step 111, it is determined if an instruction has been issued by the user to discard the component 18 used for the creation of transfer inspection data H and L, and if it is determined that an instruction to discard the component 18 has been issued, continuing to step 112, post-transfer component 18 used for the creation of transfer inspection data H and L is discarded, processing continues to step 115 of FIG. 5, and production starts.

In contrast, in step 111, if it is determined that an instruction to discard component 18 has not been issued, processing continues to step 113 and the component 18 used for the creation of transfer inspection data H and L is mounted on circuit board 22 as is, processing continues to step 115, and production starts.

On the other hand, after starting this program, if it is determined in step 101 that transfer-recognition-use/image-processing-error-determination-use transfer inspection data H and L have been set, processing continues to step 114 of FIG. 5, it is determined whether an operator has operated production start switch 38, and if it is determined that production start switch 38 has not been operated, the state becomes standby until that operation is performed. After that, at the point when an operator operates production start switch 38, continuing to step 115, production starts. In step 115, component 18 is picked up by suction nozzle 19 and the component 18 is moved to within the field of view of component imaging camera 21.

Then, continuing to step 116, the shutter speed of component imaging camera 21 is set to the shutter speed obtained in step 108, the bottom surface of pre-transfer component 18 held by suction nozzle 19 is captured by component imaging camera 21, that image is gray processed, and the pre-transfer bump 20 portion pixel values are obtained and stored in storage device 34.

Then, continuing to step 117, after solder has been transferred to each bump 20 on the bottom surface of component 18 by component 18 held by suction nozzle 19 being moved above rotation table 15 of transfer device 14 and then being lowered, component 18 is moved within the field of view of component imaging camera 21. Then, continuing to step 118, in the same way as step 116, the shutter speed of component imaging camera 21 is set to the shutter speed obtained in step 108, the bottom surface of post-transfer component 18 held by suction nozzle 19 is captured by component imaging camera 21, that image is gray processed, and the post-transfer bump 20 portion pixel values are obtained and stored in storage device 34.

Then, continuing to step 119, the post-transfer bump 20 portion pixel value is compared with transfer-recognition-use transfer inspection data H to inspect whether solder transfer is good/bad, and the post-transfer bump 20 portion pixel value is compared with image-processing-error-determination-use transfer inspection data L to determine whether an image processing error occurred, then, continuing to step 120, it is determined whether a solder transfer defect or image processing error occurred, and if a solder transfer defect and image processing error has not occurred, continuing to step 122, the post-transfer component 18 is mounted on circuit board 22. Then, production is continued by processing from step 115 being performed repeatedly.

In contrast, if a solder transfer defect or image processing error is determined to have occurred in step 120, processing continues to step 121 and post-transfer component 18 is discarded. Then, continuing to step 123, it is determined whether the cause of the solder transfer defect or image processing error requires the recreation of transfer inspection data H and L, and if it is determined that the recreation of transfer inspection data H and L is required, processing from step 103 of FIG. 4 is repeated, and transfer-recognition-use/image-processing-error-determination-use transfer inspection data H and L are recreated. In contrast, if it is determined that recreation of transfer inspection data H and L is not required in step 123, production is continued by processing from step 115 being performed repeatedly.

According to the above embodiment, because the functioning transfer inspection data creation device 36 is loaded on component mounter 11, transfer inspection data creation device 36 automatically determines the shutter speed used for inspecting the transfer state, and transfer inspection data H and L is created based on the pixel values of the pre- and post-transfer bump 20 portions of the images captured at that shutter speed, the work and time for creating transfer inspection data can be greatly reduced and even an operator not knowledgeable in the creation method of transfer inspection data H and L can easily create transfer inspection data H and L. Further, as well as it being possible to acquire multiple pre-transfer images and multiple post-transfer images at multiple different shutter speeds without discarding the one component 18 used for creating transfer inspection data H and L, it is possible to use the component 18 used for creating transfer inspection data H and L as is in production, so the component 18 discard quantity can be zero or one only. Also, even if the quantity of component mounters 11 that have a transfer inspection device 37 increases, it is possible to easily create transfer inspection data H and L that absorbs the variance in lighting conditions between each component mounter 11.

Further, in the present embodiment, when determining the shutter speed to be used for inspecting the transfer state, because the shutter speed is determined as the minimum shutter speed from the shutter speeds for which the minimum value for the pixel values of the post-transfer bump 20 portion for the captured image was equal to or larger than a predetermined value, the shutter speed can be minimized within a range in which the ability to recognize the transfer state is maintained, thus meeting the demand for high speed image processing. However, the present disclosure is not limited to the case in which the shutter speed is determined as the minimum shutter speed within a range in which the ability to recognize the transfer state is maintained, for example, the shutter speed may be determined as the shutter speed which is the second-smallest, third-smallest, and so on, shutter speed within a range in which the ability to recognize the transfer state is maintained.

Also, in the present embodiment, in cases in which the production mode is set as a production mode for mounting solder transfer components and transfer inspection data automatic creation mode, because transfer inspection data H and L are created when transfer inspection data H and L have not been set, in cases in which transfer inspection data H and L required for production has not been created, production is started after transfer inspection data H and L have been automatically created.

Further, because transfer inspection data H and L are recreated when it is judged that a transfer defect or image processing error has occurred during production, in cases in which false determination of a transfer defect or image processing error occurs during production due to deviation of transfer inspection data H and L, by recreating transfer inspection data H and L, transfer inspection data H and L are corrected, thus false determination of transfer defects and image processing errors can be avoided.

Note that, the material transferred to bumps 20 on the bottom surface of component 18 is not restricted to solder, it may be any fluid out of flux, conductive paste, or adhesive. Also, transfer device 14 loaded on component mounter 11 is not limited to a rotating type transfer device equipped with rotation table 15 as shown in FIG. 1, a linear type transfer device in which the transfer table is fixed and the squeegee is moved in a straight line horizontally or in which the squeegee is fixed and the transfer table is moved in a straight line horizontally may be used.

Further, the present disclosure may be embodied with various changes which do not exceed the scope of the claims, such as the calculation method of the transfer inspection data may be changed appropriately, and so on.

REFERENCE SIGNS LIST

11: component mounter; 12: set table; 13: component supply device; 14: transfer device; 15: rotation table (transfer table); 16: squeegee; 17: mounting head; 18: component; 19: suction nozzle; 20: pump; 21: component imaging camera; 22: circuit board; 31: control device; 35: image processing unit; 36: transfer inspection data creation device (image processing means, shutter speed determining means, transfer inspection data creation means); 37: transfer inspection device

The invention claimed is:
1. A component mounter comprising:
a conveyor configured to convey a circuit board;
a suction nozzle configured to hold a component;
a camera configured to image a bump on a bottom surface of the component held by the suction nozzle; a transfer device configured to hold fluid that is one of solder, flux, conductive paste, and adhesive; and
a control device configured to image the bump onto which the fluid is not transferred at multiple shutter speeds using the camera to acquire multiple pre-transfer images captured at the multiple shutter speeds, to transfer the fluid held by the transfer device onto the bump, and to image the bump onto which the fluid is transferred at the multiple shutter speeds to acquire multiple post-transfer images captured at the multiple shutter speeds, the control device including an image processing unit, wherein
while the suction nozzle maintains suction on the component, the image processing unit is configured to determine pixel values of each of the pre-transfer images by performing gray processing on each of the pre-transfer images, and to determine pixel values of each of the post-transfer images by performing gray processing on each of the post-transfer images, the image processing unit including a transfer inspection data creation device configured to create transfer inspection data and a transfer inspection device configured to inspect a transfer state of the fluid transferred onto a bump using the transfer inspection data created by the transfer inspection data creation device, the transfer inspection data creation device includes a shutter speed determining device configured to determine a transfer state shutter speed as a minimum shutter speed from the multiple shutter speeds for which a minimum value for the pixel values of each of the post-transfer images is equal to or larger than a predetermined value, the transfer inspection data creation device is configured to create the transfer inspection data based on the pixel values of a pre-transfer image and a post-transfer image captured with the transfer state shutter speed determined by the shutter speed determining device, and the control device is configured to mount the component used for the creation of the transfer inspection data on the circuit board conveyed by the conveyor.

2. The component mounter according to claim 1, wherein the transfer inspection data creation device calculates an intermediate value between the minimum value of the pixel values of the pre-transfer image and a maximum value of the pixel values of the post-transfer image captured at the transfer state shutter speed determined by the shutter speed determining device to be used as transfer-recognition-use transfer inspection data, and the transfer inspection device uses the transfer-recognition-use transfer inspection data as a threshold value for determining fluid transfer portions and fluid non-transfer portions.

3. The component mounter according to claim 1, wherein the transfer inspection data creation device calculates a value which is smaller than a minimum value of the pixel values of the post-transfer image captured at the transfer state shutter speed determined by the shutter speed determining device by a predetermined value as image-processing-error-determination-use transfer inspection data, and the transfer inspection device uses the image-processing-error-determination-use transfer inspection data as a threshold value for determining image processing errors.

4. The component mounter according to claim 1, wherein the transfer inspection data creation device, in cases in which production is performed using components onto which fluid is transferred, creates the transfer inspection data when the transfer inspection data has not been created.

5. The component mounter according to claim 1, wherein the transfer inspection data creation device recreates the transfer inspection data when the transfer inspection device determines that a transfer defect or image processing error has occurred during production using a component onto which fluid is transferred.

6. The component mounter according to claim 1, after the transfer inspection data is created, the suction nozzle holds the component used for the creation of the transfer inspection data while the camera images the component using the transfer state shutter speed determined by the shutter speed determining device and the component is mounted on the circuit board.

* * * * *